United States Patent [19]
Facon et al.

[11] Patent Number: 5,541,078
[45] Date of Patent: Jul. 30, 1996

[54] ANTIGENIC PEPTIDE SEQUENCE OF ECHINOCOCCUS GRANULOSUS AND DIAGNOSTIC APPLICATIONS

[75] Inventors: Brigitte Facon, Compiegne; Mustapha Chamekh, Lille; Colette Dissous, Sainghin en Melantois; André Capron, Phalempin; André Tartar, Vitry-en-Artois; Héléne Gras-Masse, Merignies, all of France

[73] Assignees: Institut Pasteur, Paris Cedex; Institut Pasteur de Lille, Lille Cedex; Institut National de la Sante et de la Recherche Medicale (Inserm), Paris Cedex, all of France

[21] Appl. No.: 961,724

[22] PCT Filed: Jul. 11, 1991

[86] PCT No.: PCT/FR91/00563

§ 371 Date: Mar. 10, 1993

§ 102(e) Date: Mar. 10, 1993

[87] PCT Pub. No.: WO92/01051

PCT Pub. Date: Jan. 23, 1992

[30] Foreign Application Priority Data

Jul. 12, 1990 [FR] France .................... 90 08900

[51] Int. Cl.$^6$ .............. G01N 33/569; G01N 33/543; C07K 14; C07K 435
[52] U.S. Cl. .......... 435/7.92; 435/7.22; 435/975; 436/518; 436/536; 436/811; 530/324; 530/806
[58] Field of Search .................... 530/324, 326, 530/327, 300, 806; 424/88, 191.1, 265.1; 435/7.92, 7.22, 810, 975; 436/518, 536, 548, 811

[56] References Cited

FOREIGN PATENT DOCUMENTS

92/01051 1/1992 WIPO .

OTHER PUBLICATIONS

Biological Abstracts, vol. 88, No. 11, 1989, AN–120220, B. Hamrioui, et al., "Production of Anti–Hydatid Monoclonal Antibodies".

Molecular and Biochemical Parasitology, vol. 20, 1986, pp. 133–142, G. DiFelice, et al., "Purification and Partial Characterization of the Major Antigen of Echinococcus Granulosus (Antigen 5) with Monoclonal Antibodies".

Molecular and Biochemical Parasitology, vol. 45, Apr. 1991, pp. 233–240, B. Facon, et al., "Molecular Cloning of an Echinococcus Granulosus Protein Expressing an Immunogenic Epitope of Antigen 5".

Molecular and Biochemical Parasitology, vol. 33, 1989, pp. 171–182, L. Hemmings, et al., "The Isolation, by Differential Antibody Screening, of Echinococcus Multilocularis Antigen Gene Clones With Potential for Immunodiagnosis".

Molecular and Biochemical Parasitology, vol. 36, 1989, pp. 287–290, M. W. Lightowlers, et al., "Amino Acid Sequence Homology Between Cyclophilin and a cDNA–Cloned Antigen of Echinococcus Granulosus".

Pozzouli et al, 1975. Isolation of the most immunoreactive antigens of Echinococcus granulosus from shepp hydatid fluid. J Immunol 115:1459–1463.

Chamekh et al, 1990. Use of a monoclonal antibody specific for a protein epitope of *Echinococcus granulosus* antigen 5 in a competitive antibody radioimmunoassay for diagnosis of hydatid disease. J Immunological Meth 134:129–137.

(List continued on next page.)

*Primary Examiner*—Margaret Parr
*Assistant Examiner*—James L. Grun
*Attorney, Agent, or Firm*—Oblon, Spivak, McClelland, Maier & Neustadt, P.C.

[57] ABSTRACT

The immunogenic peptide sequence from *Echinococcus granulosus* antigen 5 is recognized both by sera from patients suffering from hydatidosis and by a monoclonal antibody of isotype IgG1 produced by hybridoma EG 02154/12 and registered with the C.N.C.M. on Jun. 25, 1990 under number 1-957.

9 Claims, 8 Drawing Sheets

OTHER PUBLICATIONS

Heath et al, 1992. Echinococcus granulosus in sheep: transfer from ewe to lamb of 'Arc 5' antibodies and oncosphere–killing activity, but not protection. Int J. Parasitol 22:1017–1021.

Bellanti, 1971. *Immunolgy*. W. B. Saunders, Philadelphia. pp. 484–487.

```
1  E F I R K Y D K G N K G K I N L E E L T A M L D S V H R K T S R A S M S R           37 Eg 14 (SEQ ID NO: 17)
                           * *** *            *              *

80 F L N T T L S E A D K A K T K L E E V R L D L D S D K T K L K N A K T A E D K A K  122 Eg 6 (SEQ ID NO: 1)
```

FIG. 2

ANTIGENIC PEPTIDE SEQUENCE OF ECHINOCOCCUS GRANULOSUS AND DIAGNOSTIC APPLICATIONS

The present invention relates to an immunogenic peptide sequence of *Echinococcus granulosus*, to a DNA sequence coding for this peptide sequence and also to the diagnostic and therapeutic applications of the peptide sequence.

BACKGROUND OF THE INVENTION

Unilocular echinococcosis or hydatidosis is a parasitic disease due to the development in man and also livestock of the larval form of a small cestode, *Echinococcus granulosus*. The dog represents the reservoir of the adult parasite. This parasitosis is a genuine scourge in breeding countries in Africa, in Latin America and in Australia, as well as the countries bordering the Mediterranean basin, where there are economic repercussions in both the medical and the veterinary field. While almost no diagnostic test is at present available for animals, medical diagnosis is often intricate on account of the non-specificity of the symptoms observed. On the other hand, several standard immunological methods, such as haemagglutination and the complement-fixation reaction, have been performed for the detection of hydatidosis. Hydatid fluid, used as a source of antigens, contains, in addition to the products of metabolism of the parasite common to other helminths, several components of the host (CAPRON A. et al. (1), RUSSI S. et al. (2), BEN-ISMAEL R. et al. (3). This gives rise to the problem of false-positive reactions. However, the almost constant presence of antibodies that precipitate an antigen designated antigen 5 has been shown by the immunoelectrophoresis technique (CAPRON A. et al. (4) and (5)). Since then, this test has remained one of the best immunological reference tests for any epidemiological study of hydatidosis. Antigen 5, which is highly immunogenic, has formed the subject of several studies showing that it is a thermolabile lipoprotein capable of binding to concanavalin A, of relative molecular mass approximately 60 kDa (ORIOL R. et al. (6), BOUT D. et al. (7), PIANTELLI M. (8)). Analysed under reducing conditions, this antigen dissociates into two subunits of 37 and 22 Dka. Using more sensitive techniques such as ELISA, the diagnostic potential of purified antigen 5 has been amply confirmed. Anti-antigen 5 antibodies have also been detected in sera of patients or animals infected with *E. multilocularis* or with other cestodes such as *Taenia hydatigena, T. ovis* and *T. solium*. However, their level remains low. These few observed false-positive reactions have been attributed in part to the presence of a phosphorylcholine epitope on antigen 5.

The current problem is to be able to have at one's disposal specific parasitic antigens which are well standardised and in sufficient quantity for the diagnostic tests. This is the standpoint from which the studies currently being carried out on hydatidosis, and which are based on monoclonal antibody and genetic engineering techniques, are endeavouring to isolate and identify parasitic components possessing a high degree of specificity.

The objective of the present invention is to provide a parasitic antigen specific to hydatidosis.

SUMMARY OF THE INVENTION

The inventors have characterised an $IgG_1$ isotype monoclonal antibody, designated EG 02 154/12, directed towards a protein epitope carried by antigen 5 and specific to *E. Granulosus*.

This monoclonal antibody has made it possible to isolate, from a complementary DNA library obtained from mRNA of *E. Granulosus* protoscolex, clones designated Eg 6 and Eg 14, corresponding to peptide sequences which were shown to be recognised by the monoclonal antibody EG 02 154/12.

The subject of the present invention is consequently an immunogenic peptide sequence of antigen 5 of *Echinococcus granulosus*, characterised in that it is recognised both by sera of patients suffering from hydatidosis and by an $IgG_1$ isotype monoclonal antibody produced by the hybridoma EG 02 154/12 deposited at the CNCM on 25 Jun. 1990 under No. 1-957.

The subject of the present invention is also a DNA sequence comprising the nucleotide sequence designated EG 6, (SEQ ID No: 15)

```
        10        20        30        40        50        60
GAATTCGTAGACATCAACATTGCATCTAAAGTCGCGGATGCTTTCCAGAAGAATAAGGAG 70        80        90       100       110       120
AAGATTACTACTACCGACAAACTGGGTACTGCTCTCGAGCAGGTTGCTTCCCAATCAGAA 130       140       150       160       170       180
AAGGCAGCTCCCCAACTTTCTAAAATGCTGACGGAAGCTTCTGATGTCCATCAGCGTATG 190       200       210       220       230       240
GCCACTGCCAGAAAGAATTTCAATAGTGAGGTTAATACCACCTTCATTGAAGATTTGAAA 250       260       270       280       290       300
AACTTCTTGAACACCACGCTTAGCGAGGCCCAGAAAGCAAAGACCAAGCTGGAGGAGGTT 310       320       330       340       350       360
CGACTAGATTTGGACTCTGACAAGACTAAATTGAAGAATGCTAAGACTGCGGAACAGAAG 370       380       390       400       410       420
GCCAAGTGGGAGGCCGAGGTGCGAAAAGACGAAAGTGACTTCGATCGAGTGCACCAAGAA
```

```
                430         440         450
                 |           |           |
            TCTCTTACTATCTTTGAGAAGACTTGCAAAGAATTC
```

The subject of the present invention is also the immunogenic peptide sequence of antigen 5 of *E. Granulosus*, designated peptide sequence Eg 6, encoded by the above nucleotide sequence, comprising all or part of the sequence (SEQ ID No: 1)

GluPheValAspIleAsnIleAlaSerLysValAlaAspAlaPheGlnLysAsnLysGlu

LysIleThrThrThrAspLysLeuGlyThrAlaLeuGluGlnValAlaSerGlnSerGlu

LysAlaAlaProGlnLeuSerLysMETLeuThrGluAlaSerAspValHisGlnArgMET

AlaThrAlaArgLysAsnPheAsnSerGluValAsnThrThrPheIleGluAspLeuLys

AsnPheLeuAsnThrThrLeuSerGluAlaGlnLysAlaLysThrLysLeuGluGluVal

ArgLeuAspLeuAspSerAspLysThrLysLeuLysAsnAlaLysThrAlaGluGlnLys

AlaLysTrpGluAlaGluValArgLysAspGluSerAspPheAspArgValHisGlnGlu

SerLeuThrIlePheGluLysThrCysLysGluPhe as well as the sequences which differ therefrom by one or more amino acids and which possess similar immunogenic activity.

From the sequence of the clone EG 6, it is possible to envisage the synthesis of 13 peptides whose sequences correspond, respectively, to amino acids 1 to 25 (SEQ ID NO:2), 12 to 34 (SEQ ID NO:3), 22 to 44 (SEQ ID NO:4),

```
           10              20              30              40
     GAA TTC ATT CGA AAG TAT GAC AAG GGC AAT AAA GGC AAG ATC AAC 50              60              70              80              90
     TTG GAA GAG TTG ACT GCT ATG CTC GAC AGT GTT CAT AGA AAA ACC 100             110             120             130
     AGT AGA GCC TCA ATG AGC CGA TGA AGC ATT TAA AAT TAT GAG AAT
```

35 to 48 (SEQ ID NO:5), 41 to 63 (SEQ ID NO:6), 46 to 65 (SEQ ID NO:7), 60 to 91 (SEQ ID NO:8), 66 to 96 (SEQ ID NO:9), 89 to 122 (SEQ ID NO:10), 93 to 115 (SEQ ID NO:11), 98 to 129 (SEQ ID NO:12) 118 to 152 (SEQ ID NO:13) and 130 to 152 (SEQ ID NO:14) and are as follows:
EFVDINIASKVADAFQKNKEKITTT (SEQ ID NO:2)
ADAFQKNKEKITTTDKLGTALEQ (SEQ ID NO:3)
ITTTDKLGTALEQVASQSEKAAP (SEQ ID NO:4)
VASQSEKAAPQLSK (SEQ ID NO:5)
KAAPQLSKMLTEASDVHQRMATA (SEQ ID NO:6)
LSKMLTEASDVHQRMATARK (SEQ ID NO:7)
MATARKNFNSEVNTTFIEDLKNFLNTTLSEAQ (SEQ ID NO:8)
NFNSEVNTTFIEDLKNFLNTTLSEAQKAKTK (SEQ ID NO:9)
EAQKAKTKLEEVRLDLDSDKTKLKNAKTAEQKAK (SEQ ID NO:10)
AKTKLEEVRLDLDSDKTKLKNAK (SEQ ID NO:11)
EEVRLDLDSDKTKLKNAKTAEQKAKWEAEVRK (SEQ ID NO:12)
EQKAKWEAEVRKDESDFDRVHQESLTIFEKTCKEF (SEQ ID NO:13)
KDESDFDRVHQESLTIFEKTCKEF (SEQ ID NO:14)

Special preference is given to the sequence 89 to 122:
EAQKAKTKLEEVRLDLDSDKTKLKNAKTAEQKAK (SEQ ID NO:10)

The corresponding peptide, designated 89/122, is especially advantageous since it displays a strong homology in respect of the secondary structure ($\alpha$-helix) with the peptide sequence obtained from a clone Eg 14 selected from the cDNA library of *E. Granulosus*, whose nucleotide sequence (SEQ ID NO:16) is as follows:

Another subject of the invention is also a DNA sequence comprising the sequence of the clone EG 14, above.

The subject of the invention is also the immunogenic peptide sequence of antigen 5 of *E. Granulosus* encoded by Eg 14, comprising all or part of the sequence (SEQ ID NO:17)

E F I R K Y D K G N K G K I N

L E E L T A M L D S V H R K T

S R A S M S R as well as the sequences which differ therefrom by one or more amino acids and which possess similar immunogenic activity.

In the present invention, the inventors in the first place obtained a complementary DNA Eg 6 by the following operations:

extraction of the RNA of *E. Granulosus* protoscolices, production of single-stranded complementary DNA from the messenger RNA, then of double-stranded complementary DNA, insertion into a vector such as bacteriophage $\lambda$gt11, screening of the library and selection of positive recombinant clones, transfer of the selected cDNA to a phage vector in order to amplify it, purify it and carry out the sequencing thereof.

The peptide sequences according to the invention may be obtained by conventional peptide synthesis, by the use of the Applied Biosystems method or by application of genetic engineering techniques, comprising the insertion of a DNA sequence coding for a peptide sequence according to the invention into an expression vector such as a plasmid, and the transformation of cells with this expression vector.

The subject of the present invention is hence also plasmids and expression vectors comprising a DNA sequence coding for a peptide sequence according to the invention, as well as hosts transformed with this vector.

The subject of the present invention is also a process for the in vitro diagnosis of hydatidosis in man or in animals, by the demonstration of antibodies directed towards an immunogenic peptide sequence as defined above in a biological sample of human or animal origin, in which the peptide sequence or sequences is/are brought into contact with the biological sample of human or animal origin which may contain the said antibodies, and the presence of the bound antibodies is visualised.

This process may be based on a radioimmunological method of the RIA, RIPA or IRMA type, or an immunoenzymatic method of the WESTERN BLOT type on strips or of the ELISA type.

The subject of the present invention is also a kit for the in vitro diagnosis of hydatidosis, for carrying out the process mentioned above, comprising at least one immunogenic peptide sequence as described above and containing, in addition, an antibody specific for an immunoglobulin isotype.

The subject of the present invention is also a vaccine intended for the treatment and prevention of hydatidosis in man or animals, in which the vaccinating agent consists of an immunogenic peptide sequence as defined above.

Apart from the immunogenic peptide sequence, the vaccine can contain an adjuvant endowed with immunostimulatory properties.

The adjuvants which may be used include inorganic salts such as aluminium hydroxide, hydrophobic compounds or surfactants such as Freund's incomplete adjuvant, squalane or liposomes, synthetic polynucleotides, microorganisms or components of microorganisms such as murabutide, synthetic artificial molecules such as imuthiol or levamisole, or alternatively cytokines such as α-, β- and γ-interferons or interleukins.

The subject of the invention is, in addition, a monoclonal antibody directed towards an immunogenic peptide sequence as defined above.

The monoclonal antibodies according to the invention may be prepared according to a conventional technique. For this purpose, the polypeptides may be coupled, if necessary, to an immunogenic agent, such as tetanus anatoxin, with a coupling agent such as glutaraldehyde, a carbodiimide or bis-diazotised benzidine.

Special preference is given to the Ig $G_1$ subclass monoclonal antibody obtained from the hybridoma EG 02 154/12 deposited at the CNCM on 25 Jun. 1990 under No. 1-957, which also constitutes a subject of the invention.

The following will be described below in greater detail:
the production of the antibody EG 02 154/12
the production of the cDNA Eg 6 (SEQ ID NO:15) and the cDNA Eg 14 (SEQ ID NO:16) coding for the peptide sequences according to the invention.

BRIEF DESCRIPTION OF THE FIGURES

FIG. 2 shows the homologies between the amino acid sequence of the clone Eg14 and that of the clone Eg6. Identical amino acids are indicated by an asterisk;

Figure 5:
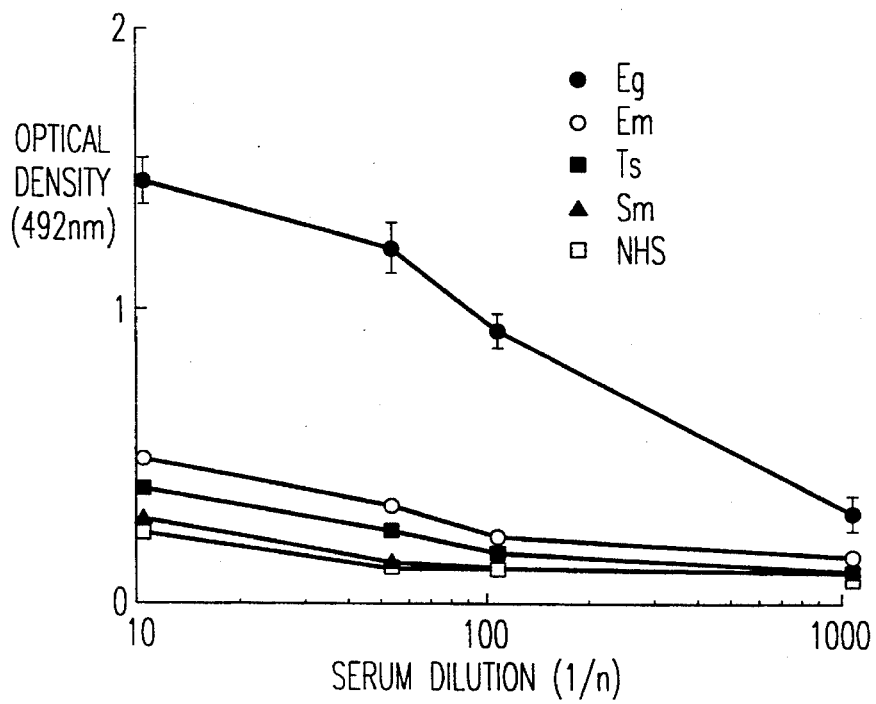

A peptide corresponding to the antigen of the hepatic stage of infection with *P. falciparum* (LSA) was used as a control;

FIG. 5 shows the reactivity of the IgG-A-M of miscellaneous human sera with the synthetic peptide 89–122 used in the form of solid-phase antigen in an ELISA test. The results represent the mean ± standard deviation of 4 different human sera: anti-*E.granulosus* (Eg), anti-*E.mutilocularis* (Em), anti-*T.saginata* (Ts) and anti-*S.mansoni* (Sm), and of normal human sera (NHS).

Figure 6:
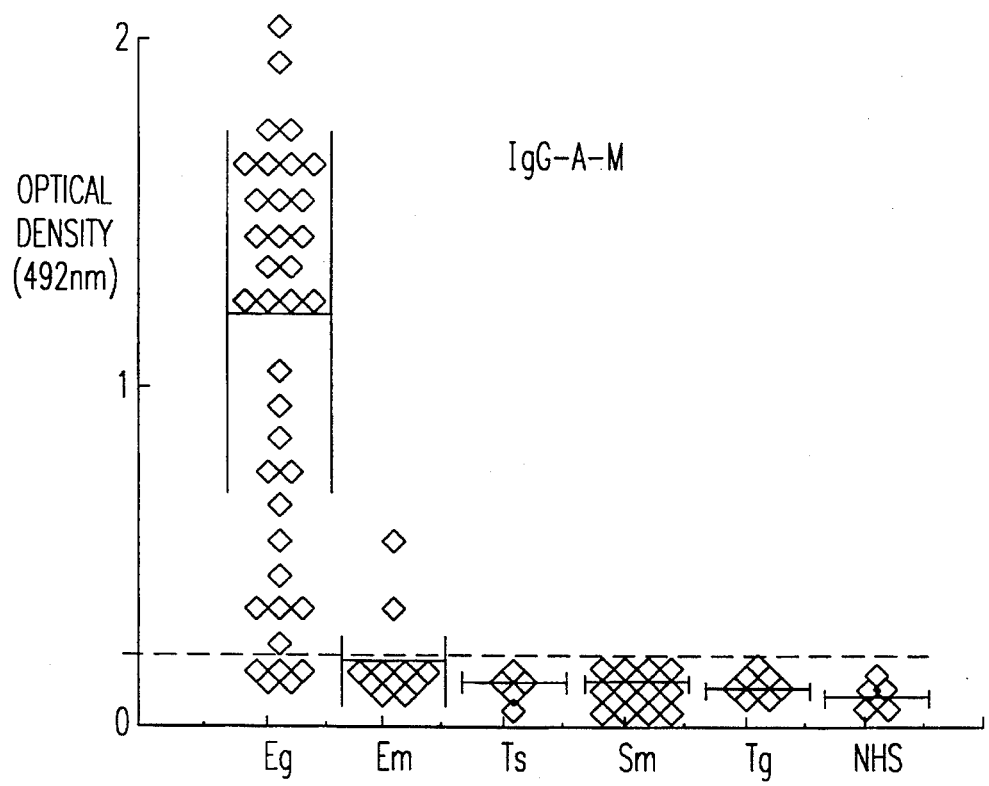
Figure 7:
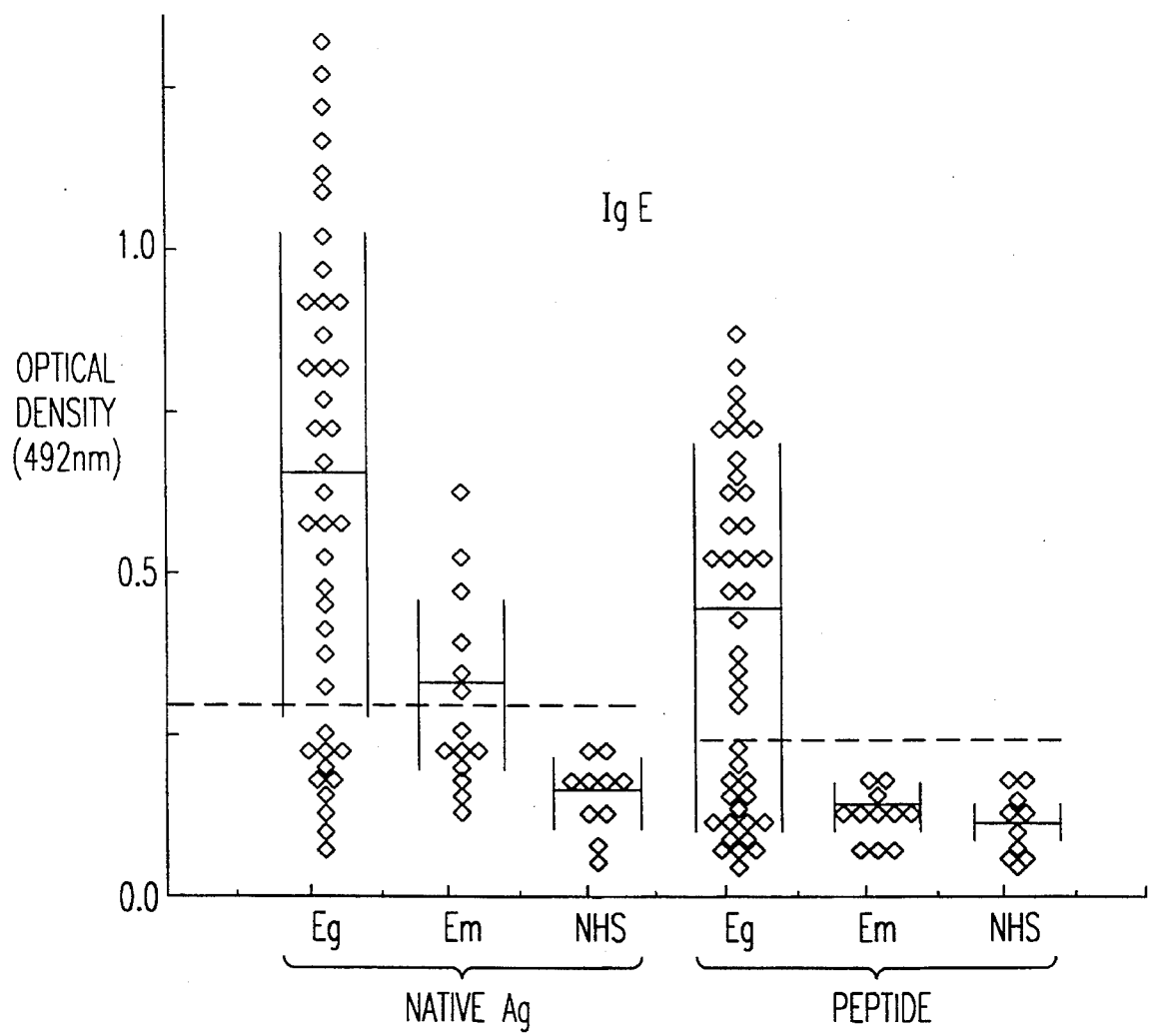

FIG. 6 shows the distribution of the reactivity of IgG-A-M of sera of patients infected with *E.granulosus* (Eg), *E.multilocularis* (Em), *T.saginata* (Ts), *S.mansoni* (Sm) and *T.gordii* (Tg) and of normal human sera (NHS) with the peptide 89–122 (SEQ ID NO:10) in an ELISA test. The line (---) represents the cut-off line, determined using a mean obtained from sera of controls (unexposed individuals living in France; N=10) plus 3 standard deviation values;

FIG. 7 shows the distribution of the reactivity of IgE in an ELISA test of sera of patients infected with *E.granulosus* (Eg), *E.multilocularis* (Em) and *T.saginata* (Sm) and of normal human sera (NHS) with the peptide 89–122 and antigens of hydatid cyst fluid (native antigens); the values above the line (---) corresponding to the cut-off line (mean of 10 control sera+3 standard deviation values) were considered to be positive.

DETAILED DESCRIPTION OF THE INVENTION

I/ Preparation of the Monoclonal Antibodies EG 02 154/12

BALB/C mice were immunised intraperitoneally with 100 g of an antigenic preparation (SHFAg) obtained by the aseptic tapping of sheep hydatid fluids from hydatid cysts removed from the animal's liver and lungs, which were assembled, ultracentrifuged at 40,000 rpm, then lyophilised and taken up in Freund's complete adjuvant (v/v).

Two weeks after the last injection, a booster injection was given to the mice with 100 μg of the SHF Ag antigenic preparation in saline solution. After 3 days, the spleen cells were harvested, and then fused with SP 2/0 myeloma cells at a ratio of 1/5 in polyethylene glycol (PEG 1500) according to the technique described by GALFRE et al. (9). The cells were distributed in wells on microculture plates, and the fused cells selected in a HAT (hypoxanthine aminopterin thymidine) medium. The culture supernatants of each well showing a dense growth of hybdrid cells were tested by an ELISA method for the presence of antibodies directed towards the SHF Ag antigenic preparation.

Among several monoclonal antibodies reacting positively in the ELISA tests with the SFH Ag antigenic preparation, a hybrid cell line (EG 02 154/12) producing Ig $G_1$ subclass antibodies was chosen. In contrast to rabbit serum directed towards a total SHF antigenic preparation, the monoclonal antibody EG 02154/12 showed in immuno-electrophoresis a single precipitation line corresponding to antigen 5 as defined from human hydatid sera of patients infected with *E. granulosus*.

No precipitation was observed with the antigens of *E. multilocularis* cyst fluid.

The positive wells were cloned by limiting dilution. Mouse ascitic fluids to which hybridoma cells were added were fractionated by ammonium sulphate precipitation followed by filtration on Trisacryl GF 05 gel (LKB, Sweden). The monoclonal antibodies were purified by ion exchange chromatography on DEAE-Trisacryl (LKB, Sweden) and dialysed against 10 mM phosphate-buffered saline solution (PBS).

II/ Production of the Complementary DNA

1. Obtaining the Sera

The sera of patients were subjected to the standard immunodiagnostic tests for echinococcosis: immunoelectrophoresis (IEP) and haemagglutination test. They are characterised with respect to *E.granulosus* and *E. multilocularis*. The presence of arc 5 in IEP is decisive for the diagnosis of *E.granulosus* infection. The diagnosis is, moreover, confirmed by medical examination and surgery and/or therapeutic treatment.

2. Preparation of the Parasites

The parasitic material is harvested in sheep. The hydatid cysts are removed from the animal's liver or lungs and tapped aseptically. The protoscolices are prepared by decantation of the liquid collected. The sedimentation pellet is taken up and washed several times with physiological fluid. The scolices are recovered each time after sedimentation. They are then frozen directly in a minimum volume of liquid nitrogen.

3. Extraction of the RNA from the *E.granulosus* Protoscolices

The total RNA is extracted from the parasitic larvae according to a modified protocol of the technique of CHIRGWIN J. et al. (10). The preparations of *E.granulosus* protoscolex stored in liquid nitrogen are ground manually before being taken up in a solution of 4.2M guanidium thiocyanate, 2% N-lauroylsarcosine, 10 mM EDTA pH 8, 5% 2-mercaptoethanol and 20 mM sodium acetate pH 4.5. This preparation is homogenised (Ultraturax) before being sonicated and centrifuged at 10,000 rpm for 20 min (Sorvall-rotor HB-4). The supernatant is then placed on a cushion of 2 ml of caesium chloride solution (CsCl, density=1.72, 10 mM EDTA pH 8, 50 mM sodium acetate pH 5.5). The tubes are centrifuged at 28,000 rpm (Beckman-rotor SW41) for 20 hours at 20° C. The RNA pellet is then taken up in water and precipitated with absolute ethanol at −20° C.

4. Preparation of the cDNA Library in Phage Lambda gt11 Vector

Starting with 300 µg of total RNA extracted from *E.granulosus* protoscolices, the complementary DNA strand is synthesised through the action of reverse transcriptase by means of an oligo-dT primer. The RNA is then attacked with ribonuclease H, which perforates it. The remaining pieces of RNA then serve as initiators for the action of *E. coli* DNA polymerase I, which consequently synthesises the second strand of the cDNA. The use in the final phase of T4 DNA polymerase enables the portions which are still single-stranded to be digested in order to create a blunt-ended complementary DNA. The protocol and the reagents needed for the synthesis of the cDNA are supplied by Amersham International ("cDNA synthesis system" kit), as are the enzymes for cloning in the phage vector. The EcoRI sites of the cDNA are then protected by methylation using the action of EcoRI methylase. Dephosphorylated double-stranded synthetic octanucleotides (Amersham International) of sequence 5'-GGAATTCC-3' are attached to the blunt ends of the cDNA using T4 DNA ligase. The EcoRI sites of the bonding segments are then liberated by EcoRI digestion. The excess bonding segments are removed by column chromatography (Amersham International). The cDNA thus prepared is integrated in the EcoRI site of phage λgt11 (YOUNG R. and DAVIS R. (11)) marketed by Promega Biotec in EcoRI-digested and dephosphorylated form. After ligation, the phages are encapsidated in vitro ("Packagen in vitro packaging system" system—Promega Biotec). The library is then tested by inoculation of *E. Coli* strain Y1090 as described by YOUNG R. and DAVIS R. (12).

5. Screening of the Library and Selection of Positive Recombinant Clones

A sample of this library in gt11 is inoculated into *E. Coli* strain Y1090 at a concentration of $5 \times 10^3$ to $8 \times 10^3$ pfu (plaque forming units)/Petri dish (90 mm in diameter). Expression of the protein is under the control of the lac promoter, and may be induced by adding IPTG (isopropyl b-D-thiogalactopyranoside). The IPTG is added by placing nitrocellulose filters (Schleicher and Schuell) impregnated with 10 mM IPTG on the Petri dishes. The proteins synthesised are adsorbed on the filter, which is then incubated with a mixture of 5 sera of patients infested with *E.granulosus*, intended for screening of the library, at a dilution of 1/100 (at 4° C.—overnight) in PBS buffer (phosphate buffer saline: 10 mM $Na_2HPO_4$, 10 mM $NaH_2PO_4$, 150 mM NaCl). Sera were chosen on the basis of their immunoelectrophoretic characteristics (from 3 to 6 arcs including arc 5 in conventional IEP). The filters are then washed and the bound antibodies are recognised with a second, anti-human immunoglobulin antibody (anti-IgG, A, M) labelled with peroxidase (Pasteur Production—1/500) and visualised with the reagent 4-chloro-1-naphthol (Bio Rad).

Of the $1.5 \times 10^6$ recombinants constituting the library, approximately $5 \times 10^5$ phages were tested: 13 clones synthesising a protein or protein fraction carrying epitopes recognised by the mixture of patients' sera were selected. Electrophoretic analysis in agarose gel enabled the size of the cDNA inserts to be measured for each of them: clone 1: an insert of 130 bp, clone 2: 138 bp, clone 3: 216 bp, and for the other ten clones an insert of 456 bp.

A second screening of the library permitted isolation of a 14th clone (Eg14; SEQ ID NO:16) synthesising a protein or protein fraction containing epitopes recognised by the monoclonal antibody EG 02 154/12. Electrophoretic analysis in agarose gel showed that the cDNA insert contained 137 bp and possessed a single open reading frame in frame with gt11, coding for 37 amino acids.

6. Hybridisation Test

After cloning into the EcoRI site of the vector M13mp18, the cDNA insert of the clone 6 (Eg 6—456 bp; SEQ ID NO:15) was purified and used as a probe in a hybridisation test.

In order to avoid all problems of background, the cDNA insert used as a probe was integrated beforehand in the EcoRI site of the vector M13mp18, and then purified from an M13 recombinant clone. The probe (60–80 ng) was prepared and labelled using [$^{32}$P]-dCTP employing the technique of FEINBERG and VOGELSTEIN (13). The clones were cultured and deposited on the same Petri dish in the form of a drop with individual identification of each clone. The DNA was then adsorbed on nitrocellulose directly from the lytic plaques and prepared according to the protocol of MASON and WILLIAMS (14).

Hybridisation was carried out according to the conditions described by WAHL et al. (15), at 42° C. using 5×10$^7$ cpm of the probe in question. Washes were performed under highly stringent conditions at 65° C. in 0.1×SSC buffer, 0.1% SDS (SSC×20: 3M NaCl, Na$_3$ citrate.2H$_2$O, adjusted to pH 7), this being done in order to test for the strictest homologies.

No signal was demonstrated with respect to the clones 1, 2 and 3, suggesting that the latter possess a sequence different from the insert 6. In contrast, the clones 4 to 13 are seen to hybridise with the probe in question, suggesting similar sequences. An analysis of the nucleotide sequences confirmed, moreover, the strict identity of the clones 4 to 13.

7. Determination of the Nucleotide Sequence and Corresponding Protein Sequence

The total phage DNA of the clones is prepared according to the technique described in MANIATIS T. et al. (16), then digested with EcoRI and analysed by electrophoresis on low-melting agarose gel. The cDNA inserts are extracted by the hot phenol technique. They are then integrated in phage vector M13mp18 (Amersham International). After transformation of E.coli strain TG1, the single-stranded templates of the recombinant vectors are prepared. The sequencing technique is based on the dideoxynucleotide chain termination principle as described by SANGER F. et al. (17) and using photoluminescent primers (Applied Biosystems). The fluorescence of the DNA fragments is detected with a 370 A DNA Sequencer (Applied Biosystems) automatic sequencer, and the nucleotide sequences are accordingly determined as described by SMITH L. et al. (18). The corresponding protein sequences are then deduced by computer analysis (PC Gene software). The sequence homologies are tested for by computer and consultation of the Swissprot. (Switzerland) and NBRF (National Biomedical Research Fondation, Washington D.C.) databases.

The cDNA insert of the clone 6 (SEQ ID NO:15) of E.granulosus was subcloned into phage vector M13mp18 and the nucleotide sequence was determined (456 bp). The 5' and 3' ends probably correspond to internal EcoRI sites, not protected during the cDNA methylation reaction, where the sequences of the bonding segments were not to be found. A single open reading frame was detected, in frame with the lambda vector, to which a polypeptide chain of calculated molecular weight 17.3 kDa corresponds. The nucleic acid and protein sequences (SEQ ID NO:15 and 1, respectively) have been shown above. Computer analysis indicates an alpha-helical (to the extent of more than 90%) secondary structure of the peptide in question. Two glycosylation sites were found, present on amino acids 72 and 84. Sequence homologies were tested for by consultation of the databases. The highest degree of homology (20% out of 117 AA) was obtained by comparison with the heavy chain of rabbit skeletal muscle myosin (AA 100 to 216) and the heavy chain b of rabbit cardiac muscle myosin (AA 508 to 620).

The cDNA insert of the clone 14 of E. granulosus was subcloned and sequenced according to a protocol strictly identical to that used for the clone 6.

8. Lysogenic Construction—Expression of the Fusion Protein

Lysogenic constructions are obtained by infecting E.coli strain Y 1089 bacteria as described by YOUNG R. & DAVIES (12) with 5 times as many gt11 phages of the clone in question. This bacterial strain possesses the lac repressor (lac I gene product) which inhibits expression of the fusion protein until IPTG is introduced into the medium. It makes it possible, in addition, by virtue of its characteristics (hfl A 150 (high frequency lysogeny)—sup F$^-$), to obtain the lysogenic phase in the phage. The lysogenic colonies are selected for their character of temperature sensitivity (the repressor of the phage becomes non-functional at 42° C.). Bacterial lysates containing the fusion protein are prepared according to the protocol described by HUYNTH T. et al. (19).

After selection of the recombinant lysogenic colonies for the clone 6, expression of the fusion protein was induced and the lysogenic extracts were prepared. SDS-polyacrylamide gel analysis showed an apparent molecular weight of 133 kDa for the fusion protein in question (FP6), corresponding, in fact, to the expected molecular weight of the fusion of a 152-AA polypeptide with β-galactosidase.

9. SDS-polyacrylamide Gel Electrophoresis and Immunoblotting

The lysogenic extracts are analysed on SDS-polyacrylamide gel according to the conditions described by LAEMMLI U.—(21) under reducing conditions using a 3% concentrating gel and a 7% separating gel. The gels are stained after electrophoresis with Coomassie blue or subjected to an electrotransfer according to the conditions of TOWBIN et al. (20). After saturation with 3% milk/PBS, the nitrocellulose is incubated overnight at 4° C. with sera of patients infested with E.granulosus and E.multilocularis with 1% milk/PBS. After washes, a second, peroxidase-labelled specific antibody is incubated (Pasteur Production—anti-human Ig 1/500, anti-mouse IgG 1/500). Visualisation is performed under the same conditions as were described above in point 7 for the screening of the library. The human sera are diluted in PBS from 1/100 to 1/500. The monoclonal antibody EG 02154/12 is diluted from 1/50 to 1/100 according to the immunoglobulin concentration. The sera are always incubated beforehand with a total extract of E.coli protein as well as a solution of purified b-galactosidase (Sigma) in order to decrease the background.

A partial proteolytic degradation was observed in these tests. Eleven of the 14 human anti-E.granulosus sera (equivalent to 80% of the sera tested) recognise the recombinant 133-kDa protein as well as, strongly, another molecule of 81 kDa, probably corresponding to a degradation product. A secondary band of 104 kDa was also visualised more weakly. The same bands were detected with 9 of the sera of E. multilocularis infection.

Subsequently, the immunoreactivity of the fusion protein was analysed with respect to the monoclonal antibody against antigen 5, EG 02 154/12. This antibody showed recognition of the 133-kDa recombinant protein FP6, and also of two other molecules of 104 kDa and 81 kDa, degradation products of the first protein. Analysed under the same conditions, a human serum specific in IEP for antigen 5 (one arc=arc 5) likewise recognised the bands of 133, 104 and 81 kDa. On the other hand, the monoclonal antibody EG 02 154/12 and the sera of infection were tested with respect to the protein components of *E. coli* and purified β-galactosidase, without any band of molecular mass corresponding to the degradation products or to the fusion protein being visualised.

10. Synthesis of the Peptides

The peptides were synthesised according to a discontinuous solid-phase method (22) in an automatic peptide synthesis apparatus (Applied Biosystems model 430a, Fester city, Calif.) according to the BOC-TFA (butoxy-carbonyltrifluoroacetate) protocol on a benzhydrylamine type resin (Applied Biosystems). The trifunctional amino acids were protected in the following manner: Arg (Tos), Asp (OBzl), Glu (OBzl), Lys (2-ClZ (chlorobenzyloxycarbonyl)), Ser (OBzl). The amino acids were introduced following activation with a symmetrical anhydride in DMF (single coupling), except in the case of Gln, which was introduced using the DCC/HOBt (dicyclocarbodiimide/butanol) activation protocol. The final deprotection and cleavage of the peptidyl resins were carried out according to a process involving a high HF content, for one hour at 0° C. The deprotected, cleaved peptide was precipitated with cold diethyl ether, then dissolved in acetic acid at 100° C. and lyophilised. The crude peptide was purified by gel filtration (TSK HW40S, MERCK), followed by reversed-phase HPLC chromatography on a Nucleosil C18, 300 Å 5.5µ column (Macherey Nagel) (12.7 mm×500 mm) using a high-resolution gradient over 3 hours, from a buffer A1 (0.05% trifluoroacetic acid in water) to 60% of a buffer B1 (0.05% trifluoroacetic acid/75% acetonitrile/25% water) with a flow rate of 2 ml/mm. The hydrochloride form of the peptide was obtained using a stepwise gradient, from a buffer A2 (pH 3 HCl in water) to a buffer B2 (pH 3 50% HCl/50% isopropanol) on a Nucleosil C18, 300 Å, 5µ column (12.7 mm×75 mm). The peptides were analysed with respect to their homogeneity by reversed-phase analytical HPLC, and with respect to their identity by an amino acid analysis and a determination of molecular mass.

The helical organisation may be suitably mimicked by long peptides (Gras-Masse et al. (24)).

Figure 1A:
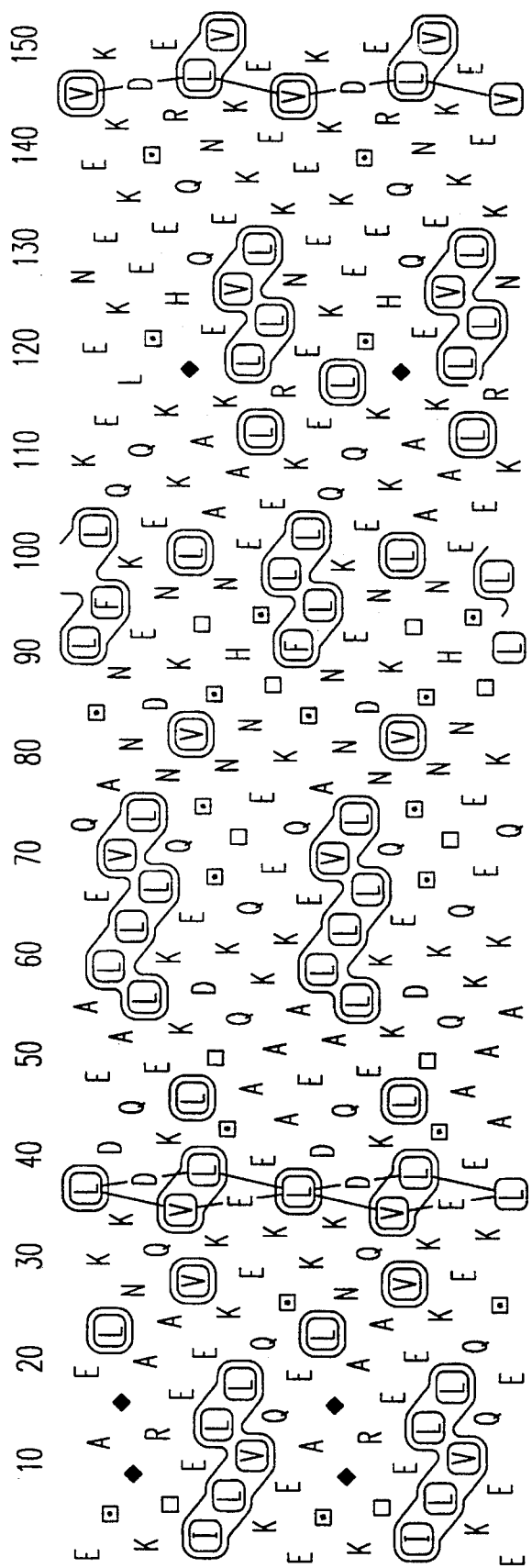
FIGS. 1A–1C illustrate the representation obtained after analysis of the hydrophobic groups (hydrophobic cluster analysis (HCI)) of the heavy chain of rabbit skeletal muscle myosin (FIG. 1A), and the recombinant proteins Eg6 (FIG. 1B) and Eg14 (FIG. 1C). Adjacent hydrophobic residues are ringed. Some residues are represented by the symbols: (P(*) (G(♦) T(□) S(▣)). The homology of topographic units between Eg6 and Eg14 is in hatched lines.
Figure 1B:
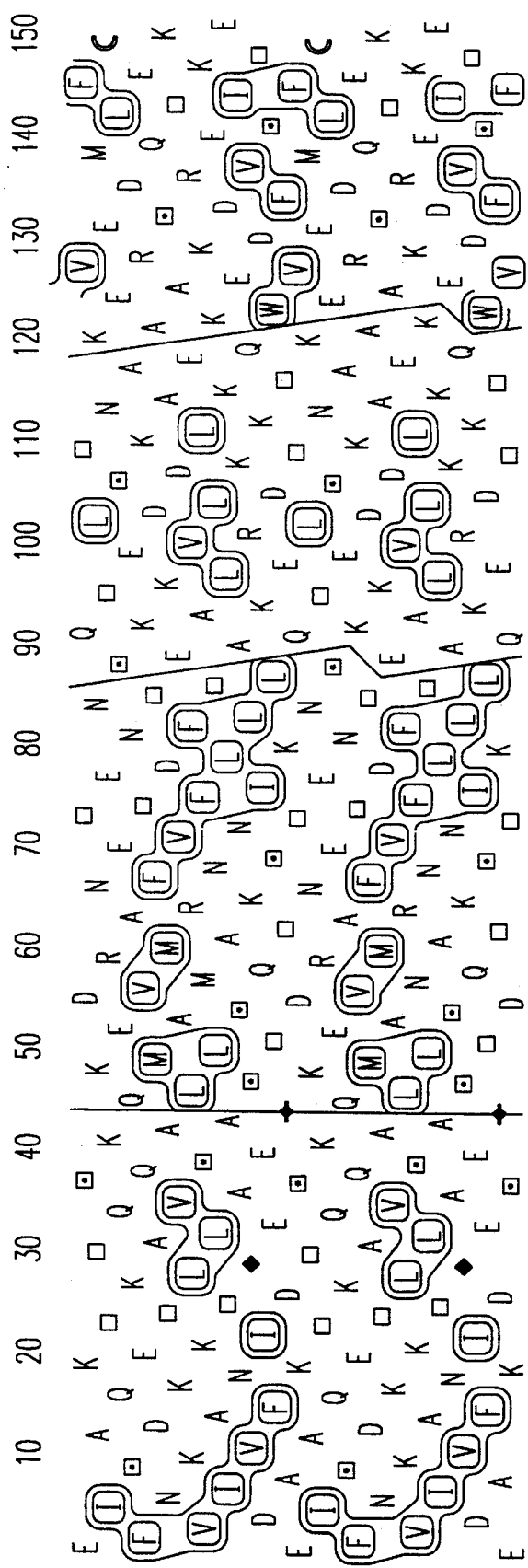
Figure 1C:
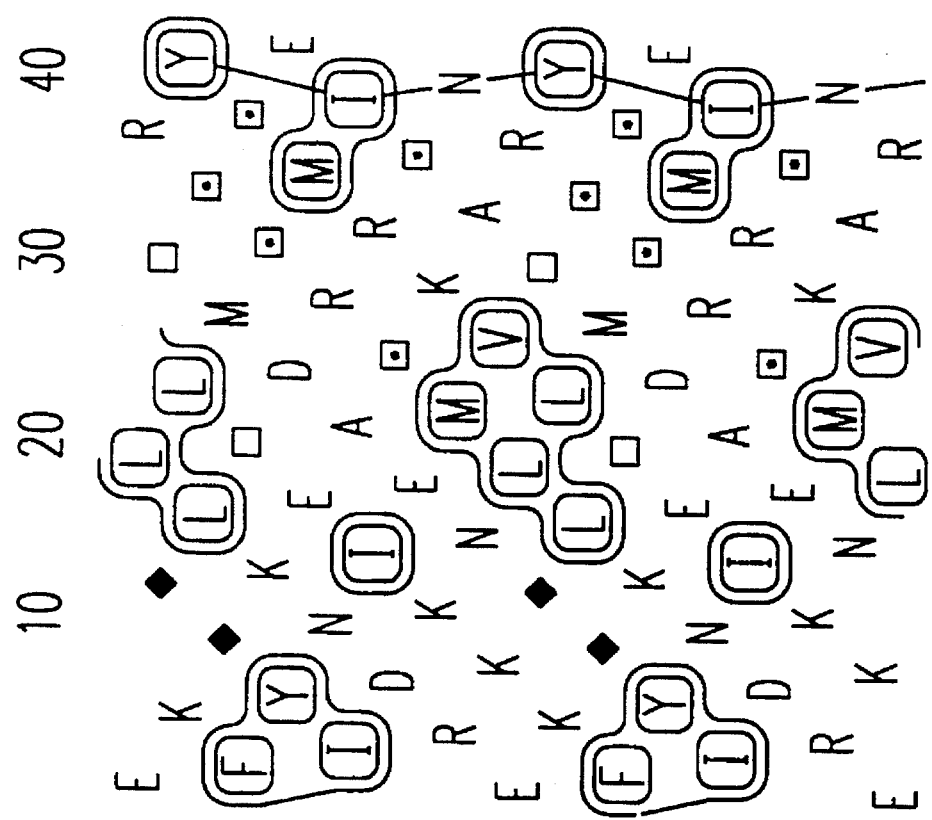

The sequences of Eg6 and Eg14 were represented using the hydrophobic cluster analysis technique described by LEMESLE-VAROOT (23) FIGS. 1B and 1C. This technique, as well as other more conventional techniques for predicting secondary structure, suggests organisation in the form of a helical band. The longitudinal distribution of the hydrophobic group along the helical band is strongly reminiscent of a coiled helical structure such as that of the heavy chain of rabbit skeletal muscle myosin (FIG. 1A).

Besides their common structural properties, the clones Eg14 (SEQ ID NO:16) and Eg6 (SEQ ID NO:15) display limited sequence homologies (FIG. 2). However, in the graphic representation, these discontinuous sequence homologies form topographic units present on both fragments which may explain the cross-reactivity observed with Eg 02 154/12. In addition, the high proportion of polar or charged residues in these homologous structures may argue in favour of their presence in predominantly exposed regions of the native antigen.

Consequently, the inventors selected and synthesised a peptide of 34 amino acids, reproducing the sequence of the clone Eg6 from amino acid 89 to amino acid 122 (FIG. 2; SEQ ID NO:10) and bringing together the two homologous units (FIG. 1B). In order to introduce stabilising charge interactions between the ends of this peptide designated 89–122 and the dipole of the helix (Schoemaker et al. (25)), they introduced a negatively charged glutamic acid residue at the N-terminal end and a positively charged lysine residue at the C-terminal end.

11. Study of Circular Dichroism (CD)

The CD spectra were recorded on a ROUSSEL JOUAN 185 model II apparatus at room temperature. The peptide concentrations were adjusted from stock solutions by quantitative amino acid analysis after total acid hydrolysis. The CD studies were carried out on the hydrochloride forms of the peptide, at a concentration of 10 mM in 200 mM NaCl with an optical path length of 0.1 mm, or at a concentration of 1 mM in 1 mM trifluoroethanol with an optical path length of 1 mm. The CD results were expressed in terms of mean helical structure of the residue ($\theta$) expressed in deg.d-mol$^{-1}$.cm$^2$. The helix content was calculated from the CD spectra, taking ($\theta$) 222=−35.700 deg.dmol$^{-1}$.cm$^2$ for 100% of helical structure.

Figure 3:
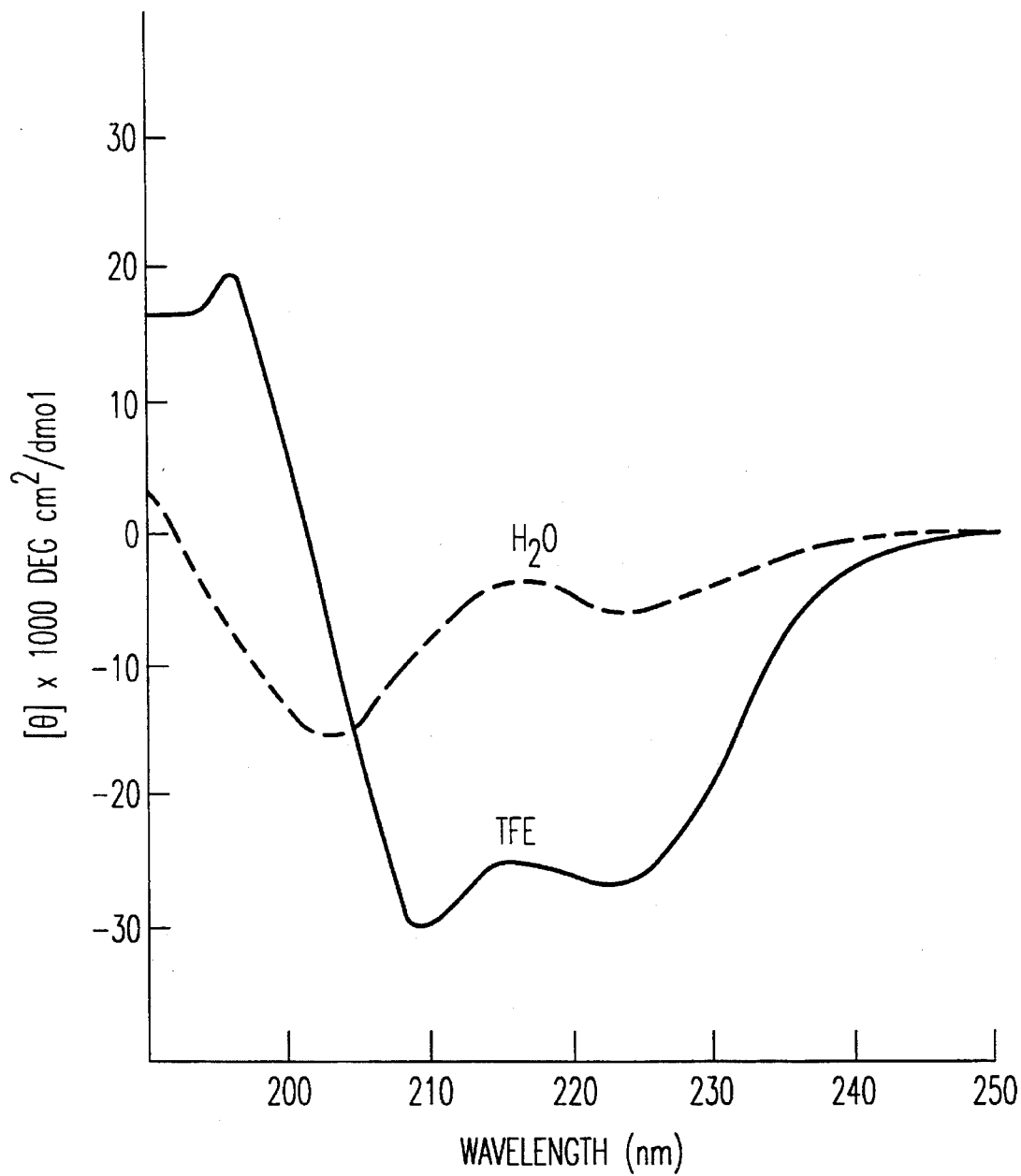
FIG. 3 shows the circular dichroism spectra of the peptide 89–122 in water and trifluoroethanol (TFE)

The helical organisation of the peptide was verified by circular dichroism studies carried out at room temperature in an aqueous solution or an aqueous solution of trifluoroethanol. The results illustrated in FIG. 3 show that both spectra are characteristic of a helical organisation, with minima at 202–207 nm and 222–223 nm and a positive value at around 290 nm. Taking $\theta_{222}$=−35.700 deg.$^2$cm$^2$/dmol for 100% of helical structure, a helical proportion of 14% in aqueous solution and a helical proportion of 74% in aqueous trifluoroethanol were found.

12. ELISA and Inhibition Tests

Plates (Nunc) were coated with 100 µl of Ag of hydatid cyst fluid or of bacterial extract (lysogen (FP6)) in the proportion of 5 µg/ml of proteins. The human sera were used at a 1/100 dilution, and the bound antibodies were detected using anti-human IgG-A-M conjugated with HRP (horseradish peroxidase) (DIAGNOSTICS PASTEUR). Human sera and the antibody EG 02 154/12 were preincubated overnight at 4° C. with different concentrations of synthetic peptides. The ELISA test with IgE was carried out with human sera diluted to 1/10 in phosphate-buffered saline solution, and the peptide 89/122 was spread in the proportion of 1 µg per well. Mouse anti-(human IgE) IgG$_1$ was obtained by Southern Biotechnology Associates Inc. (Birmingham, United Kingdom). The values obtained (mean or doublet) were expressed as the optical density (OD) at 492 nm±standard deviation (SD).

The results obtained with the peptide Eg 6 in the diagnosis of hydatidosis are given below.

The peptide 89–112 (SEQ ID NO:10) of Eg 6 bound directly to PVC microplates is fully recognised by the monoclonal antibody EG 02 154/12 as well as by the sera of patients infected with *E. granulosus* in an ELISA test, as indicated by the measurement of the optical densities in Table I below. A good correlation was obtained between the recognition of the fusion protein FP6 by the antibodies and their binding to the peptide Eg 6 (SEQ ID NO:1).

TABLE I

| sera and ascites diluted to 1/100 | mean of the ± optical densities | standard deviation |
|---|---|---|
| hydatid sera recognising FP6 (n = 25) | 1.96 | 0.57 |

TABLE I-continued

| sera and ascites diluted to 1/100 | mean of the ± optical densities | standard deviation |
|---|---|---|
| hydatid sera not recognizing FP6 (n = 5) | 0.77 | 0.11 |
| normal human sera (n = 5) | 0.22 | 0.07 |
| monoclonal antibody (ascites EG 02 154/12) | 3.4 | 0.3 |
| myeloma ascites (SP2/0) | 0.12 | 0.04 |

Figure 4A:
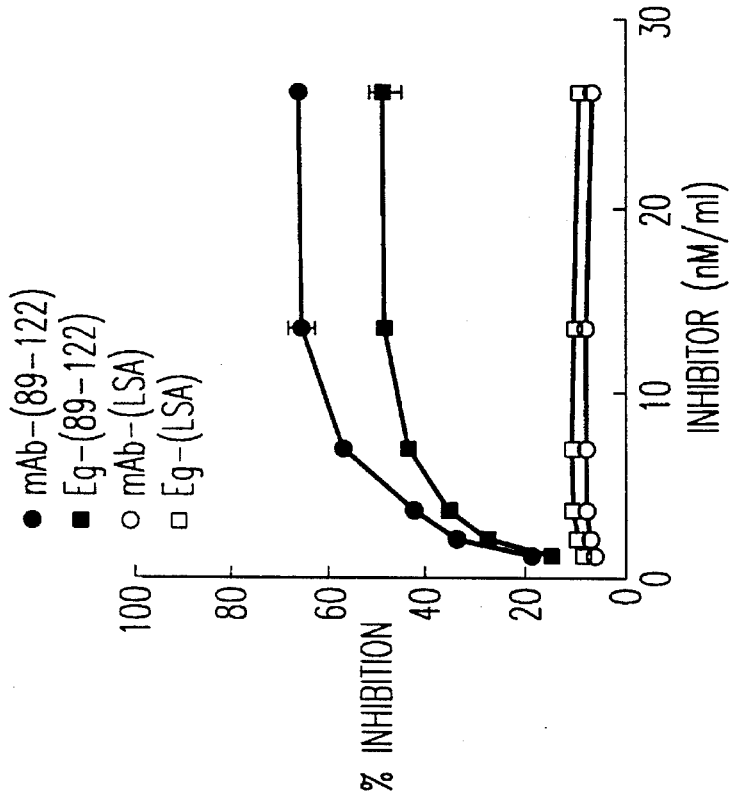
FIGS. 4A and 4B show the curves of inhibition of binding of the monoclonal antibody Eg 0-2 154/12 (mAb) and of human sera of patients suffering from hydatidosis (Eg) to the fusion protein FP6 (FIG 4A) or to the antigens of hydatid cyst fluids (FIG. 4B) by the synthetic peptide 89–122 (SEQ ID NO:10)
Figure 4B:
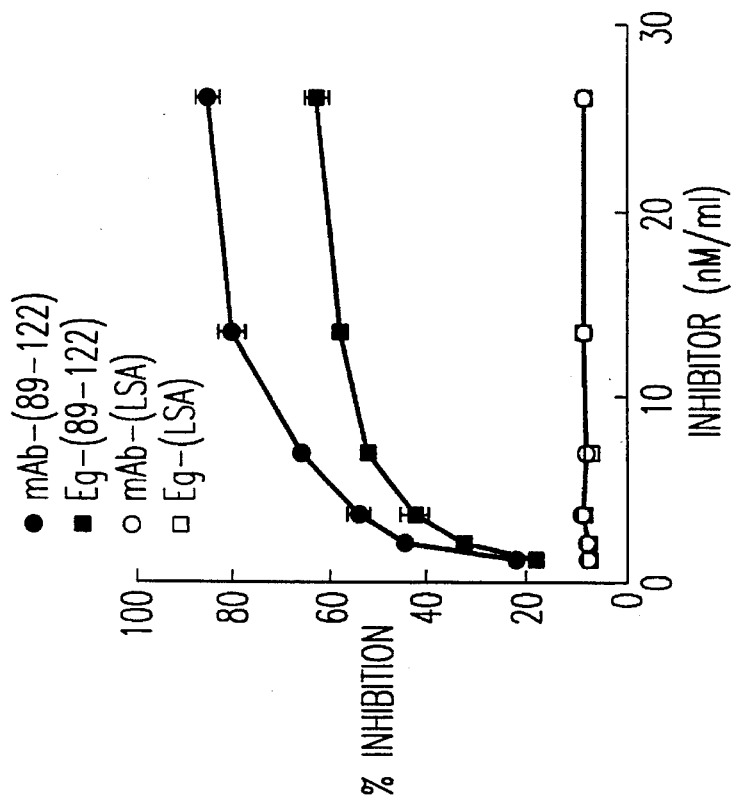

Furthermore, the inhibitory power of this peptide in the binding of the monoclonal antibody EG 02 154/12 and of human sera of patients suffering from hydatidosis with respect to the protein FP6 or to antigen of hydatid cyst fluid was measured in an ELISA test. As shown in FIG. 4A, substantial inhibitions of the binding of the monoclonal antibody (80%) and of human sera of patients suffering from hydatidosis (60%) to the protein FP6 were obtained with the peptide 89–122. This peptide is also capable of significantly inhibiting the binding of these antibodies to the antigens of hydatid cyst fluid (65 and 45%, respectively (FIG. 4B). The inhibition of binding is more effective for the monoclonal antibody than for the human sera of patients suffering from hydatidosis. No significant inhibition is observed with an unrelated synthetic peptide (26) forming a helix (41 amino acids) corresponding to the hepatic stage of infection with *P.falciparum* (27).

These results suggest that the peptide 89–122 is capable of mimicking the binding sites specifically recognised by the monoclonal antibody Eg 02 154/12 and the human sera of patients suffering from hydatidosis.

The reactivity of sera of patients infected with *E.granulosus* or other parasites with respect to the peptide 89–122 used as bound antigen was also measured, in an ELISA test.

Using different dilutions of sera, it is observed that significant binding to the antibody takes place only with anti-*E.granulosus* sera, as shown in FIG. 5. The levels of binding of anti-*E.multilocularis,* anti-*T.saginata* and anti-*S.mansoni* sera were lower than the values obtained with normal human sera.

In tests with an unrelated synthetic peptide, all these sera showed similar levels of response.

ELISA tests were also carried out to demonstrate the immunodiagnostic value of the peptide 89–122. Two types of human antibody (IgG-A-M and Ig-E) response were analysed. Using the defined upper limit of positive values, three standard deviation values above the mean obtained from the control group, a high sensitivity of binding (85%) and good specificity (86%) are observed in the IgG-A-M response (FIG. 6). These results were compared with those obtained in Western blot tests with FP6 and an improvement in the specificity was observed, which shows the special advantage 89–122 in the diagnosis of hydatidosis. The results are presented in Table II below.

TABLE II

| | IgG-A-M-WM*-FP6 | peptide 89-122 in ELISA test | | | |
|---|---|---|---|---|---|
| | | positive IgG-A-M sera | | positive IgE sera | |
| Human sera | no. (%) positive | no. (%) | OD (492 mm) mean ± SD | no. (%) | OD (492 nm) mean ± SD |
| hydatidosis (n = 40) | 34 (85) | 34 (85) | 1.18 ± 0.52 | 24 (60) | 0.7 ± 0.24 |
| Alveolar echinococcosis | 4 (28.5) | 2 (14) | 0.4 ± 0.14 | 0 (0) | — |
| Taeniasis (T. saginata) (n = 5) | 1 (20) | 0 (0) | — | 0 (0) | — |
| Schistosomiasis (n = 18) | 2 (11) | 0 (0) | — | 0 (0) | — |
| Toxoplasmosis (n = 15) | 0 (0) | 0 (0) | — | 0 (0) | — |
| Normal human serum (n = 10) | 0 (0) | 0 (0) | — | 0 (0) | — |

*Carried out by Western blot test using a peroxidase-conjugated anti-IgG-A-M.

As shown in this table, the IgE response with respect to the peptide 89–122 shows a high specificity (100%) for patients infected with *E.granulosus*. No IgE type reactivity could be detected with 52 sera obtained from patients suffering from other parasitic diseases, while 60% of the human sera of patients suffering from hydatidosis (24/40) proved positive in this IgE-ELISA test. A control test carried out with an unrelated synthetic peptide (LSA) showed no significant activity in the two ELISA tests.

The sensitivity and specificity of this test were compared with ELISA-IgE tests carried out with total antigens of hydatid fluid (FIG. 7). The reactivity of the IgE with respect to the peptide 89–122 seems to be more specific (100%) for *E.granulosus,* while 32% (6 out of 19) of the sera infected with cestodes showed a cross-reaction with antigens of hydatid cyst fluid. The IgE antibodies of 29 out of 40 (72% of patients infected with *E.granulosus*) reacted with the antigens of hydatid fluid. The sensitivity of the ELISA-IgE observed with the peptide 89–122 (60%) remains great in comparison with that obtained with the native hydatid antigens.

| Symbols for the amino acids | | |
|---|---|---|
| A | Ala | alanine |
| C | Cys | cysteine |
| D | Asp | aspartic acid |
| E | Glu | glutamic acid |
| F | Phe | phenylalanine |
| G | Gly | glycine |
| H | His | histidine |
| I | Ile | isoleucine |
| K | Lys | lysine |
| L | Leu | leucine |
| M | Met | methionine |
| N | Asn | asparagine |
| P | Pro | proline |
| Q | Gln | glutamine |
| R | Arg | arginine |
| S | Ser | serine |
| T | The | threonine |
| V | Val | valine |
| W | Trp | tryptophan |
| Y | Tyr | tyrosine |

REFERENCES

1—Capron A., Biguet J., Vernes A. and Afchain D. (1968) Structure antigénique des helminthes. Aspects immunologiques des relations hôte-parasite. (Antigenic structure of helminths. Immunological aspects of the host-parasite relationships.) Pathologie Biologie 16, 121

2—Russi S., Siracusano A., Remy G., Dropsy G. (1974) Isolation and characterization of blood P1 active carbohydrate antigen of Echinococcus granulosus cyst membrane. Journal of Immunology 112, 1061

3—Ben-Ismael R., Carme B., Niel G., Gentilini M. (1980) Non-specific serological reactions with Echinococcus granulosus antigens. Rôle of anti-P1 antibodies. American Journal of Tropical Medicine and Hygiene 19, 239

4—CAPRON A., VERNES A & BIGUET J. (1967) In: Les Journées Lyonnaises d'hydatidologie (Ed. SIMEP), 27–40

5—Capron A., Yarzabal L., Vernes A., Fruit J. (1970) Le diagnostic immunologique de l'echicococcose humaine. (bilan personnel à propos de 400 observations) [Immunological diagnosis of human echicococcosis. (personal assessment on the basis of 400 observations)] Pathologie Biologie 18, 357

6—Oriol R., Williams J. F., Peres Escandi M. V., Oriol (1971) Purification of lipoprotein antigens of Echinoccus granulosus from sheep hydatid fluid. American Journal of Tropical Medicine and Hygiene 20, 569

7—Bout D., Fruit J., Capron A. (1974) Purification d'un antigène spécifique du liquide hydatique. (Purification of an antigen specific to hydatid fluid.) Annales de l'institut Pasteur (Immunology) 125C, 775

8—Piantelli M., Pozzuoli R., Arru E., Musiana P. (1977) Echinococcus granulosus: Identification of subunits of major antigens. Journal of Immunology 119, 1382

9—Galfre B. M., How S. C., Milstein C., Butcher G. W., Howard J. C. (1977) Antibodies to major histocompatibility antigens produced by hybrid cell lines. Nature 266, 550

10—CHIRGWIN J. M., PRZYBYLA A. E., MAC DONALD R. J. & RUTTER W. J. (1979) Biochem. 18 (24), 5294–5299

11—YOUNG R. A. & DAVIS R. W. (1983) Proc. Natl. Acad. Sci. USA 80, 1194–1198

12—YOUNG R. A. & DAVIS R. W. (1983) Science 22, 778–782

13—FEINBERG A. P. & VOGELSTEIN B. (1983) Ann. Biochem 132, 6–13

14—MASON P. J. & WILLIAMS J. G. (1985) In: A Practical Approach, Ed. B. D. Hames & S. I. Higgins, IRL Press, 113–137

15—WAHL G. M., STERN M. & STARKG R. (1979) Proc. Natl. Acad. Sci. USA 76(8), 3683–3687

16—MANIATIS T., FRITSCH E. F. & SAMBROOK J. (1982) In: Molecular Cloning: A Laboratory Manual, Ed. Cold Spring Harbor Laboratory, 545 p.

17—SANGER F., NICKLEN S. & COULSON A. R. (1977) Proc. Natl. Acad. Sci. USA 74 (12) 5463–5467

18—SMITH L. M., SANDERS J. ZJ, KAISER R. J., HUGHES P., DOON C., CONNEL C. R., HEINER C., KENT S. B. H. & HOOD L. E. (1986) Nature 321, 674–679

19—HUYNH T. V., YOUNG R. A. & DAVIS R. W. (1985) In: DNA Cloning Techniques (volume I): A Practical Approach, Ed. D. M. Glover, IRL Press, Oxford 20—Towbin H., Staehelin T., Gordon J. (1979) Electrophoretic transfert of proteins from polyacrylamide gels to nitrocellulose sheets: Procedure and some applications. Proceedings of the National Academy of Sciences (USA) 76, 4350

21—Laemmli U. K. (1970) Cleavage of structural proteins during the assembly of the head of the bacteriphage T4. Nature 227, 680

22—Merrifield R. B. 1963. Solid-phase peptide synthetis. The synthesis of a tetrapeptide. J. Am. Chem. Soc. 85:2149–2155

23—Lemesle-Varloot L., B. Henrissat, C. Gaboriaud, V. Bissery, A. Morgat and J. P. Mornon. 1990. Hydrophobic cluster analysis: procedures to derive structural and functional information from 2-D-representation of protein sequences. Biochimie. 72:555–574

24—Gras-Masse H., M. Jolivet, H. Drobecq, J. F. Aubert, E. H. Beachey, F. Audibert, L. Chedid and A. Tartar. 1988. Influence of helical organization on immunogenicity and antigenicity of synthetic peptides. Mol. Immunol. 25: 673–678

25—Shoemaker K. R., P. S. Kim, E. J. York, J. M. Stewart and R. L. Bladwin. 1987. Tests of the helix dipole model for stabilization of α-helices. Nature. 326: 563–565

26—Arturo Londono J., Gras-Masse H., C. Dubeaux, A. Tartar and P. Druilhe. 1990. Secondary structure and immunogenicity of hybrid synthetic peptides derived from two Plasmodium falciparum pre-erythrocytic antigens. J. Immunol. 145: 1557–1563

27—Guerin C., P. Druilhe, B. Galey, J. A. Londono, J. Patarapotikul, R. L. Beaudoin, A. Tartar, O. Mercereau-Puijalon and G. Langsley. 1987. A liver-stage-specific antigen of Plasmodium falciparum characterized by gene cloning. Nature 329: 164–169

We claim:

1. An antigenic peptide having an amino acid sequence consisting of SEQ ID NO:10.

2. A process for the in vitro diagnosis of hydatidosis in a human or animal, comprising contacting a biological sample obtained from said human or animal with the peptide of claim 1 under conditions wherein antibodies in the sample specifically bind to the peptide, and conducting a radioimmunological or immunoenzymatic assay to detect antibodies bound to said peptide, wherein the presence of antibodies bound to said peptide is a positive indication of hydatidosis in the human or animal.

3. The process of claim 2, wherein said assay is a radioimmunological assay.

4. The process of claim 2, wherein said assay is an immunoenzymatic assay, and said method further comprises visually detecting said antibodies bound to said peptide.

5. The process of claim 3, wherein said radioimmunological assay is selected from the group consisting of RIA, RIPA and IRMA.

6. The process of claim 4, wherein said immunoenzymatic assay is a Western blot or ELISA.

7. A kit for the in vitro diagnosis of hydatidosis, comprising the peptide of claim 1.

8. The kit of claim 7, further comprising an antibody specific for an immunoglobulin isotype.

9. The kit of claim 7, further comprising buffers and reagents for carrying out RIA, RIPA, IRMA, a Western blot or an ELISA.

* * * * *

SEQUENCE LISTING ( 1 ) GENERAL INFORMATION:

( i i i ) NUMBER OF SEQUENCES: 17

( 2 ) INFORMATION FOR SEQ ID NO: 1:

( i ) SEQUENCE CHARACTERISTICS:
        ( A ) LENGTH: 152 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i i i ) ANTI-SENSE: NO ( x i ) SEQUENCE DESCRIPTION: SEQ ID NO: 1:

```
Glu Phe Val Asp Ile Asn Ile Ala Ser Lys Val Ala Asp Ala Phe Gln
1               5                   10                  15

Lys Asn Lys Glu Lys Ile Thr Thr Thr Asp Lys Leu Gly Thr Ala Leu
            20                  25                  30

Glu Gln Val Ala Ser Gln Ser Glu Lys Ala Ala Pro Gln Leu Ser Lys
            35                  40                  45

Met Leu Thr Glu Ala Ser Asp Val His Gln Arg Met Ala Thr Ala Arg
    50                  55                  60

Lys Asn Phe Asn Ser Glu Val Asn Thr Thr Phe Ile Glu Asp Leu Lys
65                  70                  75                  80

Asn Phe Leu Asn Thr Thr Leu Ser Glu Ala Gln Lys Ala Lys Thr Lys
                85                  90                  95

Leu Glu Glu Val Arg Leu Asp Leu Asp Ser Asp Lys Thr Lys Leu Lys
                100                 105                 110

Asn Ala Lys Thr Ala Glu Gln Lys Ala Lys Trp Glu Ala Glu Val Arg
        115                 120                 125

Lys Asp Glu Ser Asp Phe Asp Arg Val His Gln Glu Ser Leu Thr Ile
        130                 135                 140

Phe Glu Lys Thr Cys Lys Glu Phe
145                 150
```

( 2 ) INFORMATION FOR SEQ ID NO: 2:

( i ) SEQUENCE CHARACTERISTICS:
        ( A ) LENGTH: 25 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( v ) FRAGMENT TYPE: N-terminal ( x i ) SEQUENCE DESCRIPTION: SEQ ID NO: 2:

```
Glu Phe Val Asp Ile Asn Ile Ala Ser Lys Val Ala Asp Ala Phe Gln
1               5                   10                  15

Lys Asn Lys Glu Lys Ile Thr Thr Thr
            20                  25
```

( 2 ) INFORMATION FOR SEQ ID NO: 3:

( i ) SEQUENCE CHARACTERISTICS:
        ( A ) LENGTH: 23 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i i i ) ANTI-SENSE: NO ( v ) FRAGMENT TYPE: internal ( x i ) SEQUENCE DESCRIPTION: SEQ ID NO: 3:

```
Ala  Asp  Ala  Phe  Gln  Lys  Asn  Lys  Glu  Lys  Ile  Thr  Thr  Thr  Asp  Lys
1                   5                        10                       15

Leu  Gly  Thr  Ala  Leu  Glu  Gln
                20
```

( 2 ) INFORMATION FOR SEQ ID NO: 4:

( i ) SEQUENCE CHARACTERISTICS:
( A ) LENGTH: 23 amino acids
( B ) TYPE: amino acid
( C ) STRANDEDNESS: single
( D ) TOPOLOGY: linear ( i i ) MOLECULE TYPE: peptide ( i i i ) HYPOTHETICAL: NO ( i i i ) ANTI-SENSE: NO ( v ) FRAGMENT TYPE: internal ( x i ) SEQUENCE DESCRIPTION: SEQ ID NO: 4:

```
Ile  Thr  Thr  Thr  Asp  Lys  Leu  Gly  Thr  Ala  Leu  Glu  Gln  Val  Ala  Ser
1                   5                        10                       15

Gln  Ser  Glu  Lys  Ala  Ala  Pro
                20
```

( 2 ) INFORMATION FOR SEQ ID NO: 5:

( i ) SEQUENCE CHARACTERISTICS:
( A ) LENGTH: 14 amino acids
( B ) TYPE: amino acid
( C ) STRANDEDNESS: single
( D ) TOPOLOGY: linear ( i i ) MOLECULE TYPE: peptide ( i i i ) HYPOTHETICAL: NO ( i i i ) ANTI-SENSE: NO ( v ) FRAGMENT TYPE: internal ( x i ) SEQUENCE DESCRIPTION: SEQ ID NO: 5:

```
Val  Ala  Ser  Gln  Ser  Glu  Lys  Ala  Ala  Pro  Gln  Leu  Ser  Lys
1                   5                        10
```

( 2 ) INFORMATION FOR SEQ ID NO: 6:

( i ) SEQUENCE CHARACTERISTICS:
( A ) LENGTH: 23 amino acids
( B ) TYPE: amino acid
( C ) STRANDEDNESS: single
( D ) TOPOLOGY: linear ( i i ) MOLECULE TYPE: peptide ( i i i ) HYPOTHETICAL: NO ( i i i ) ANTI-SENSE: NO ( v ) FRAGMENT TYPE: internal ( x i ) SEQUENCE DESCRIPTION: SEQ ID NO: 6:

Lys Ala Ala Pro Gln Leu Ser Lys Met Leu Thr Glu Ala Ser Asp Val
1               5                   10                  15

His Gln Arg Met Ala Thr Ala
            20

( 2 ) INFORMATION FOR SEQ ID NO: 7:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i i i ) ANTI-SENSE: NO ( v ) FRAGMENT TYPE: internal ( x i ) SEQUENCE DESCRIPTION: SEQ ID NO: 7:

Leu Ser Lys Met Leu Thr Glu Ala Ser Asp Val His Gln Arg Met Ala
1               5                   10                  15

Thr Ala Arg Lys
            20

( 2 ) INFORMATION FOR SEQ ID NO: 8:

( i ) SEQUENCE CHARACTERISTICS:
        ( A ) LENGTH: 32 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i i i ) ANTI-SENSE: NO ( v ) FRAGMENT TYPE: internal ( x i ) SEQUENCE DESCRIPTION: SEQ ID NO: 8:

Met Ala Thr Ala Arg Lys Asn Phe Asn Ser Glu Val Asn Thr Thr Phe
1               5                   10                  15

Ile Glu Asp Leu Lys Asn Phe Leu Asn Thr Thr Leu Ser Glu Ala Gln
            20                  25                  30

( 2 ) INFORMATION FOR SEQ ID NO: 9:

( i ) SEQUENCE CHARACTERISTICS:
        ( A ) LENGTH: 31 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i i i ) ANTI-SENSE: NO ( v ) FRAGMENT TYPE: internal ( x i ) SEQUENCE DESCRIPTION: SEQ ID NO: 9:

Asn Phe Asn Ser Glu Val Asn Thr Thr Phe Ile Glu Asp Leu Lys Asn
1               5                   10                  15

```
    Phe  Leu  Asn  Thr  Thr  Leu  Ser  Glu  Ala  Gln  Lys  Ala  Lys  Thr  Lys
                   20                      25                      30
```

(2) INFORMATION FOR SEQ ID NO: 10:

(i) SEQUENCE CHARACTERISTICS:
    (A) LENGTH: 34 amino acids
    (B) TYPE: amino acid
    (C) STRANDEDNESS: single
    (D) TOPOLOGY: linear (ii) MOLECULE TYPE: peptide (iii) HYPOTHETICAL: NO (iii) ANTI-SENSE: NO (v) FRAGMENT TYPE: internal (xi) SEQUENCE DESCRIPTION: SEQ ID NO: 10:

```
    Glu  Ala  Gln  Lys  Ala  Lys  Thr  Lys  Leu  Glu  Glu  Val  Arg  Leu  Asp  Leu
    1                   5                        10                       15
    Asp  Ser  Asp  Lys  Thr  Lys  Leu  Lys  Asn  Ala  Lys  Thr  Ala  Glu  Gln  Lys
                   20                      25                      30
    Ala  Lys
```

(2) INFORMATION FOR SEQ ID NO: 11:

(i) SEQUENCE CHARACTERISTICS:
    (A) LENGTH: 23 amino acids
    (B) TYPE: amino acid
    (C) STRANDEDNESS: single
    (D) TOPOLOGY: linear (ii) MOLECULE TYPE: peptide (iii) HYPOTHETICAL: NO (iii) ANTI-SENSE: NO (v) FRAGMENT TYPE: internal (xi) SEQUENCE DESCRIPTION: SEQ ID NO: 11:

```
    Ala  Lys  Thr  Lys  Leu  Glu  Glu  Val  Arg  Leu  Asp  Leu  Asp  Ser  Asp  Lys
    1                   5                        10                       15
    Thr  Lys  Leu  Lys  Asn  Ala  Lys
                   20
```

(2) INFORMATION FOR SEQ ID NO: 12:

(i) SEQUENCE CHARACTERISTICS:
    (A) LENGTH: 32 amino acids
    (B) TYPE: amino acid
    (C) STRANDEDNESS: single
    (D) TOPOLOGY: linear (ii) MOLECULE TYPE: peptide (iii) HYPOTHETICAL: NO (iii) ANTI-SENSE: NO (v) FRAGMENT TYPE: internal (xi) SEQUENCE DESCRIPTION: SEQ ID NO: 12:

```
    Glu  Glu  Val  Arg  Leu  Asp  Leu  Asp  Ser  Asp  Lys  Thr  Lys  Leu  Lys  Asn
    1                   5                        10                       15
    Ala  Lys  Thr  Ala  Glu  Gln  Lys  Ala  Lys  Trp  Glu  Ala  Glu  Val  Arg  Lys
                   20                      25                      30
```

( 2 ) INFORMATION FOR SEQ ID NO: 13:

( i ) SEQUENCE CHARACTERISTICS:
        ( A ) LENGTH: 35 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i i i ) ANTI-SENSE: NO ( v ) FRAGMENT TYPE: internal ( x i ) SEQUENCE DESCRIPTION: SEQ ID NO: 13:

```
Glu Gln Lys Ala Lys Trp Glu Ala Glu Val Arg Lys Asp Glu Ser Asp
  1               5                  10                  15
Phe Asp Arg Val His Gln Glu Ser Leu Thr Ile Phe Glu Lys Thr Cys
             20                  25                  30
Lys Glu Phe
         35
```

( 2 ) INFORMATION FOR SEQ ID NO: 14:

( i ) SEQUENCE CHARACTERISTICS:
        ( A ) LENGTH: 24 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i i i ) ANTI-SENSE: NO ( v ) FRAGMENT TYPE: C-terminal ( x i ) SEQUENCE DESCRIPTION: SEQ ID NO: 14:

```
Lys Asp Glu Ser Asp Phe Asp Arg Val His Gln Glu Ser Leu Thr Ile
  1               5                  10                  15
Phe Glu Lys Thr Cys Lys Glu Phe
             20
```

( 2 ) INFORMATION FOR SEQ ID NO: 15:

( i ) SEQUENCE CHARACTERISTICS:
        ( A ) LENGTH: 456 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i i i ) ANTI-SENSE: NO ( x i ) SEQUENCE DESCRIPTION: SEQ ID NO: 15:

```
GAATTCGTAG  ACATCAACAT  TGCATCTAAA  GTCGCGGATG  CTTTCCAGAA  GAATAAGGAG     60
AAGATTACTA  CTACCGACAA  ACTGGGTACT  GCTCTCGAGC  AGGTTGCTTC  CCAATCAGAA    120
AAGGCAGCTC  CCCAACTTTC  TAAATGCTG   ACGGAAGCTT  CTGATGTCCA  TCAGCGTATG    180
GCCACTGCCA  GAAAGAATTT  CAATAGTGAG  GTTAATACCA  CCTTCATTGA  AGATTTGAAA    240
AACTTCTTGA  ACACCACGCT  TAGCGAGGCC  CAGAAAGCAA  AGACCAAGCT  GGAGGAGGTT    300
```

```
CGACTAGATT  TGGACTCTGA  CAAGACTAAA  TTGAAGAATG  CTAAGACTGC  GGAACAGAAG        360

GCCAAGTGGG  AGGCCGAGGT  GCGAAAAGAC  GAAAGTGACT  TCGATCGAGT  GCACCAAGAA        420

TCTCTTACTA  TCTTTGAGAA  GACTTGCAAA  GAATTC                                    456
```

( 2 ) INFORMATION FOR SEQ ID NO: 16:

( i ) SEQUENCE CHARACTERISTICS:
        ( A ) LENGTH: 135 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i i i ) ANTI-SENSE: NO ( x i ) SEQUENCE DESCRIPTION: SEQ ID NO: 16:

```
GAATTCATTC  GAAAGTATGA  CAAGGGCAAT  AAAGGCAAGA  TCAACTTGGA  AGAGTTGACT         60

GCTATGCTCG  ACAGTGTTCA  TAGAAAAACC  AGTAGAGCCT  CAATGAGCCG  ATGAAGCATT        120

TAAAATTATG  AGAAT                                                            135
```

( 2 ) INFORMATION FOR SEQ ID NO:17:

( i ) SEQUENCE CHARACTERISTICS:
        ( A ) LENGTH: 37 amino acids
        ( B ) TYPE: amino acid
        ( D ) TOPOLOGY: linear ( i i ) MOLECULE TYPE: peptide ( v i ) ORIGINAL SOURCE:
        ( A ) ORGANISM: Echinococcus granulosus ( x i ) SEQUENCE DESCRIPTION: SEQ ID NO:17:

```
Glu  Phe  Ile  Arg  Lys  Tyr  Asp  Lys  Gly  Asn  Lys  Gly  Lys  Ile  Asn  Leu
 1              5                         10                       15

Glu  Glu  Leu  Thr  Ala  Met  Leu  Asp  Ser  Val  His  Arg  Lys  Thr  Ser  Arg
               20                         25                       30

Ala  Ser  Met  Ser  Arg
              35
```